US009996926B2

(12) United States Patent
Leinhard et al.

(10) Patent No.: US 9,996,926 B2
(45) Date of Patent: Jun. 12, 2018

(54) LEAN TISSUE VOLUME QUANTIFICATION

(71) Applicant: Advanced MR Analytics AB, Linköping (SE)

(72) Inventors: Olof Dahlqvist Leinhard, Linköping (SE); Magnus Borga, Linköping (SE); Thobias Romu, Linköping (SE)

(73) Assignee: ADVANCED MR ANALYTICS AB, Linkoping (SE)

( * ) Notice: Subject to any disclaimer, the term of this patent is extended or adjusted under 35 U.S.C. 154(b) by 4 days.

(21) Appl. No.: 15/306,383

(22) PCT Filed: Apr. 21, 2015

(86) PCT No.: PCT/EP2015/058577
§ 371 (c)(1),
(2) Date: Oct. 24, 2016

(87) PCT Pub. No.: WO2015/162120
PCT Pub. Date: Oct. 29, 2015

(65) Prior Publication Data
US 2017/0046837 A1 Feb. 16, 2017

(30) Foreign Application Priority Data
Apr. 25, 2014 (EP) ..................................... 14165965

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/1075* (2013.01);
(Continued)

(58) Field of Classification Search
USPC ....... 382/100, 103, 106, 128–134, 154, 162, 382/168, 173, 180–181, 209, 219–220,
(Continued)

(56) References Cited

U.S. PATENT DOCUMENTS

| 2011/0091090 A1* | 4/2011 | Dahlqvist Leinhard ............ G01R 33/4828 382/131 |
| 2011/0160546 A1* | 6/2011 | Madsen ................ G06T 7/0012 600/300 |

(Continued)

FOREIGN PATENT DOCUMENTS

| WO | 2009146703 A2 | 12/2009 |
| WO | 2013086580 A1 | 6/2013 |

OTHER PUBLICATIONS

Hu, H.H., et al.; "Quantification of absolute fat mass by magnetic resonance imaging: a validation study against checmical analysis," International Journal of Body Composition Research, 2011, pp. 111-122, vol. 9.

(Continued)

*Primary Examiner* — Seyed Azarian
(74) *Attorney, Agent, or Firm* — Charles L. Moore; Michael G. Johnston; Moore & Van Allen PLLC

(57) ABSTRACT

The present invention relates to a method of quantifying a lean tissue volume comprising the steps of acquiring (10) a acquired image as a water-fat separated magnetic resonance image, wherein the acquired image comprises a water image and a fat image, providing (20) a calibrated fat image (F), providing (30) a soft tissue mask (STM) defining areas of soft tissue in the acquired image, and defining (40) a region of interest (ROI) of the acquired image. The method further comprises a step of calculating (50) a lean tissue volume (LTV) by multiplying, for each volume element in the region of interest, the soft tissue mask with the volume ($V_{vox}$) of (Continued)

each volume element and the result of one minus the calibrated fat image, and summarizing the products of said multiplications for all volume elements in the region of interest.

15 Claims, 5 Drawing Sheets

(51) Int. Cl.
| | |
|---|---|
| *A61B 5/055* | (2006.01) |
| *A61B 5/107* | (2006.01) |
| *A61B 5/00* | (2006.01) |
| *G06T 7/30* | (2017.01) |
| *G06T 7/11* | (2017.01) |
| *G06T 7/62* | (2017.01) |
| *A61B 5/05* | (2006.01) |

(52) U.S. Cl.
CPC .............. *A61B 5/4869* (2013.01); *G06T 7/11* (2017.01); *G06T 7/30* (2017.01); *G06T 7/62* (2017.01); *G06T 2207/10088* (2013.01); *G06T 2207/20128* (2013.01); *G06T 2207/30004* (2013.01)

(58) Field of Classification Search
USPC ........ 382/224, 232, 254, 274–276, 286–291, 382/305, 312, 294; 600/300, 411, 410; 378/4, 21
See application file for complete search history.

(56) References Cited

U.S. PATENT DOCUMENTS

| | | | |
|---|---|---|---|
| 2013/0137966 A1* | 5/2013 | Nakahara | A61B 5/055 600/411 |
| 2013/0243290 A1* | 9/2013 | Poonawalla | G01R 33/4828 382/131 |
| 2014/0296696 A1* | 10/2014 | Remmele | G01R 33/4816 600/410 |
| 2014/0307936 A1 | 10/2014 | Dore et al. | |

OTHER PUBLICATIONS

Hu, H.H., et al.; "Can MRI Represent an Accurate Quantitative Tool for Assessing Fat Distribution in Obesity Research?" International Society for Magnetic Resonance in Medicine, 2008, XP040607218, 1 Page.

European Patent Office; International Search Report for International Application No. PCT/EP2015/058577 dated Aug. 20, 2015, 9 Pages.

* cited by examiner

LEAN TISSUE VOLUME QUANTIFICATION

CROSS-REFERENCE TO RELATED APPLICATIONS

This application is a 35 U.S.C. § 371 National Stage Application of International Application No. PCT/EP2015/058577, filed Apr. 21, 2015, which claims the benefit of European Patent Application No. 14165965.6 filed on Apr. 25, 2014, the entirety of each of which is incorporated herein by reference.

TECHNICAL FIELD

The present disclosure relates to a method for quantification of a lean tissue volume, and especially a method for quantification of lean muscle tissue volume using a fat-water separated image from magnetic resonance imaging (MRI).

BACKGROUND

The function of the skeletal muscular system is to provide stability and to enable movement of the human body. Accurate and precise measurements of the muscle volume are therefore crucial for further understanding of different diseases, syndromes, and disorders such as muscular dystrophis, sport injuries, inflammatory myopathies, spinal cord injury or sarcopenia (muscle loss due to aging). When diagnosing sarcopenia, muscle strength tests combined with muscle volume measurements are needed. Associated to aging and the progression of sarcopenia, the composition of the muscles also changes and an increased fat infiltration occurs. However, the impact of the higher fat content inside the muscles is not yet fully understood. For improved understanding of the prevalence, onset, and progress of sarcopenia, new methods, including an accurate technique for measuring muscle volume, are needed. Another example where detailed and accurate knowledge of muscle volume and muscle composition is important is for whiplash-associated disorders (WAD). A higher fat infiltration in the neck muscles has been found in people with WAD, compared to healthy controls. A higher fat concentration in the quadriceps muscle associated to the fibromyalgia syndrome has also recently been found.

There exist many approaches for measuring human muscle mass or volume. Non-imaging methods are often highly variable as they are usually calibrated on young healthy adults. The current standard imaging method for the determination of muscle mass and its distribution is dual energy x-ray absorptiometry (DXA), which is rapid and readily available. However, DXA uses ionizing radiation and only enables analysis of two-dimensional projections of the body. Therefore, no detailed muscle group separation, or quantification of fat content within the muscle tissue, can be obtained using DXA.

A more accurate analysis can be made using tomographic methods, i.e. CT and MRI. Water-fat separated MRI, based on Dixon imaging techniques, enables a high soft tissue contrast, providing detailed measurements of the muscle volumes and fat infiltration. The drawbacks of MR imaging are its availability and cost. With current techniques, scanning the whole body with sufficient resolution for body composition analysis may be achieved in less than ten minutes. However, the workload of manually segmenting the muscle tissue within the whole body is far too great to be feasible in anything but very small studies. Even when using optimized semi-automatic methods, a single segmentation of the whole body muscular system may take several working days to complete. The development of robust automatic segmentation of muscle tissue is therefore needed in order to make MRI an attractive alternative for studying muscle tissue volume in larger studies.

Anatomical knowledge can be incorporated into a segmentation method by atlases, i.e. real or synthetic images with corresponding manually defined anatomical labels. This anatomical knowledge, i.e. the segmented atlases, can then be transferred to a new subject (target) by non-rigid registration of the atlas onto the target's images. However, due to large anatomical variation between subjects and technical difficulties such as placement of arms and legs during scanning, a single registration may not converge correctly everywhere. Therefore, most atlas-based techniques address limited parts of the body, such as the brain, which shows a relatively limited variation in shape and location of its anatomical structures.

Non-rigid registration methods maximize the similarity between two different images. The result will vary depending on the similarity measure. Two common measures are image intensity and local phase information. One example of an intensity-based method is the Demons algorithm. Another example that enables a phase-based similarity measure is the morphon method. Phase-based methods are insensitive to gradual intensity variations, which are common in MR images due to $B_0$ and RF inhomogeneity. An additional feature of the morphon is its ability to deform the prototypes on different scales with different degrees of regularization, an important feature for whole body registration.

There currently exists no method capable of providing a comprehensive and accurate description of the human skeletal muscular system that both quantifies the bulk of the muscle tissue volume and separates the muscle tissue into different muscle groups. A solution would be an important tool for studies of the interaction between phenomena such as the development of muscular atrophy, intra-muscular fat infiltration, and disease progression in a wide range of conditions including sarcopenia and muscular dystrophies.

SUMMARY

It is an object of the present invention to provide an improved solution that alleviates the mentioned drawbacks with present devices. Furthermore, it is an object to provide a method for quantification of a lean tissue volume based on a magnetic resonance image.

According to an aspect of the invention, this is provided by a method of quantifying a lean tissue volume comprising the steps of acquiring an image as a water-fat separated magnetic resonance image, wherein the acquired image comprises a water image and a fat image, providing a calibrated fat image, providing a soft tissue mask defining areas of soft tissue in the target image, and defining a region of interest of the acquired image. The method further comprises a step of calculating a lean tissue volume by multiplying, for each volume element in the region of interest, the soft tissue mask with the volume of each volume element and the result of one minus the calibrated fat image, and summarizing the products of said multiplications for all volume elements in the region of interest.

The quantification of a lean tissue volume may have the purpose of determining the volume and/or weight of the fat free tissue in the region of interest in numbers. The present invention may provide an increased accuracy in the quantification by subtracting fat signal level from the water level of the volume elements (voxels) which are present in the region of interest. The region of interest may be a specific organ, such as a muscle, a muscle group or a breast. Also diffuse fat infiltration in an organ volume may thereby be removed from the quantification. Further, only the actual fat infiltration level in a voxel may be removed from the quantification and the corresponding water level, defining for instance muscle tissue, may not be removed.

The acquired image may be a two or three dimensional magnetic resonance image. By lean tissue volume it may herein be meant a fat free tissue volume. The acquired image being a water-fat separated magnetic resonance image may comprise a water image and a fat image as an image pair.

A calibrated fat image may be provided in a plurality of known ways. For instance based on a method of proton density fat fraction (PDFF) as disclosed in Reeder, S. B., Hu, H. H. and Sirlin, C. B. (2012), Proton density fat-fraction: A standardized mr-based biomarker of tissue fat concentration. J. Magn. Reson. Imaging, 36: 1011-1014. doi: 10.1002/jmri.23741, or based on a method as described in European application EP09732976.7.

A soft tissue mask may be defined as a mask defining areas of soft tissue in the acquired image. A soft tissue mask may be provided in a plurality of known ways, for instance according to the Otsus method as disclosed in Nobuyuki Otsu (1979). "A threshold selection method from gray-level histograms". IEEE Trans. Sys., Man., Cyber. 9 (1): 62-66. doi:10.1109/TSMC.1979.4310076; and Diana Wald; Birgit Teucher; Julien Dinkel; Rudolf Kaaks; Stefan Delorme; Hans-Peter Meinzer; Tobias Heimann; Automated quantification of adipose and skeletal muscle tissue in whole-body MRI data for epidemiological studies. Proc. SPIE 8315, Medical Imaging 2012: Computer-Aided Diagnosis, 831519 (Feb. 23, 2012); doi:10.1117/12.911290.

The soft tissue mask may provide that backgrounds in the acquired image within the region of interest are removed since there is no soft tissue present. Further, the soft tissue mask may provide that bone in the acquired image within the region of interest is removed since bone is not magnetic resonance visible.

The step of calculating a lean tissue volume may be described as $$LTV = \sum_{ROI} (1 - F) \cdot STM \cdot V_{vox}$$

wherein LTV is the calculated lean tissue volume, ROI is the volume elements in the region of interest, F is the calibrated fat image, STM is the soft tissue mask and $V_{vox}$ is the volume of each voxel.

Further, a threshold for classifying a volume element at the borders of a tissue volume part of the region of interest may be lowered. At the borders, the water level (representing tissue) decrease and the fat level increase in a direction out of the tissue volume. The border is diffuse providing a gradual transition.

The quantification may be made for each volume element part of the region of interest. By determining, for each volume element, the effective, lean, tissue volume of all fat infiltration, both diffuse and pure fat infiltration, precise tissue volume quantification may be provided.

The steps for calculating the lean tissue volume in the method as described above does not necessarily need to be performed in the order presented.

In one embodiment, the method may further comprise a step of providing a calibrated water image and a step of calculating a lean tissue water concentration by multiplying, for each volume element in the acquired image, the soft tissue mask with the calibrated water image, determining a sum of the products of said multiplications for all volume elements in the region of interest, and divide said sum with said calculated lean tissue volume. The further calculation, based on the calculated lean tissue volume may provide an effective water concentration level in the region of interest as ratio of the total water and fat in the region. The effective water concentration may incorporate water visible as water signals in the magnetic resonance image, but not water or other tissue not visible in the magnetic resonance image. The calculation of the lean tissue water concentration may be described as $$LTWC = \frac{\sum_{ROI} (W \cdot STM) \cdot V_{vox}}{LTV},$$

wherein LTWC is the calculated lean tissue water concentration, ROI is the volume elements in the region of interest, W is the calibrated water image, STM is the soft tissue mask, $V_{vox}$ is the volume of each voxel and LTV is the calculated lean tissue volume as presented above. A calibrated water image may be a water image normalized with a bias field determined in a similar way as a bias field for a calibration of a fat image (see EP09732976.7). Alternatively may the water image be normalized with a bias field determined from voxels in the water image with high probability of containing fat free and water rich tissue, for instance calculated as Water/(Water+Fat)>0.9, or similar threshold, and with a sum of Water+Fat being significantly higher than a noise signal level in the water and fat signals. The calibrated water image may be determined from a water image calculated using a plurality of known methods, such as Yu H, McKenzie C A, Shimakawa A, Vu A T, Brau A C, Beatty P J, Pineda A R, Brittain J H, Reeder S B. Multiecho reconstruction for simultaneous water-fat decomposition and T2* estimation. Journal of magnetic resonance imaging: JMRI 2007; 26(4): 1153-1161.

The steps for calculating the lean tissue water concentration in the method as described above does not necessarily need to be performed in the order presented.

In one embodiment, the step of providing a soft tissue mask may comprise a step of removing volume elements that does not contain magnetic resonance visible tissue. Volume elements in the acquired image that does not contain magnetic resonance visible tissue may be removed to reduce noise around the segmented and classified muscle groups. The step of removing volume elements that does not contain magnetic resonance visible tissue may comprise the steps of providing a calibrated water image, applying a threshold to the sum of the calibrated fat image and the calibrated water image, wherein volume elements above said threshold forms a binary tissue mask, and forming a fuzzy soft tissue mask by setting the volume elements within one volume element from the borders of the binary tissue mask equal to the sum of the normalized water and fat images. Said threshold may be about 0.5. When background volume elements are removed, unclassified volume elements may be removed which otherwise may have disturbed the quantification. A more correct soft tissue mask may thereby be provided, providing more correct lean tissue quantification.

In one embodiment, the step of providing a calibrated fat image may comprises a step of consistent intensity inhomogeneity correction. Such step may be disclosed in EP09732976.7; Dahlqvist Leinhard O, Johansson A, Rydell J, et al. Quantitative abdominal fat estimation using MRI. In: Proceedings of the 19th International Conference on Pattern Recognition (ICPR'08); 2008; Tampa, Fla., USA. p 1-4. (In: Proceedings of the 19th International Conference on Pattern Recognition (ICPR'08)); or Romu T, Borga M, Dahlqvist O. MANA—Multi scale adaptive normalized averaging. In: Proceedings of the 2011 IEEE International Symposium on Biomedical Imaging: From Nano to Macro; 2011. p 361-364. (In: Proceedings of the 2011 IEEE International Symposium on Biomedical Imaging: From Nano to Macro).

Further, such step may comprise the steps of reconstructing the acquired image containing the water and fat images, wherein the reconstruction is phase sensitive such that it results in an in-phase image component (IP) comprising the water plus fat image and an out-of-phase image component (OP) comprising the water minus fat image; identifying volume elements in the reconstructed image which volume elements according to a test criterion represent pure fat tissue thus producing a pure-fat image; segmenting the pure-fat image to produce a segmented image free from non-tissue image data; and generating the intensity correction field by interpolating a fat image (F) using the volume elements indicated in the segmented image, said fat image being calculated based on the in-phase image component (IP) and the out-of-phase image component (OP). If the calibrated fat image is provided based on, for instance PDFF, there may be undefined sections at interfaces between fat and water in the acquired image, which may negatively affect the lean tissue quantification with partial volume effects. By using the steps above to provide the calibrated fat image, such drawbacks may be reduced. Furthermore effects on the calibrated fat image due to longitudinal T1 relaxation signal saturation can be effectively avoided by using the steps above as disclosed in:

Peterson, P. Quantification of Fat Content and Fatty Acid Composition Using Magnetic Resonance Imaging. Lund University Doctoral Dissertation 2013, ISBN: 978-91-87651-99-1.

In another embodiment, the step of defining a region of interest may comprise a step of non-rigid registration of at least one atlas to the acquired image to segment the acquired image. An atlas may here be defined as a water and fat image pair with corresponding anatomical information for classification of muscle groups. The atlas may be used to segment the body or body part in the acquired image into groups of organs, such as muscle groups. The non-rigid registration may be made in an automated process, providing an automated defining of the region of interest.

In one embodiment, the step of non-rigid registration may comprise a step of multi-scaled and phase-based registration of said atlas. By using a multi-scaled and phase-based registration, the atlas may be modified in order to correspond in shape with the acquired image. The atlas may be registered such that the shape of a specific, or a group of, muscle group(s) corresponds to the acquired image. The atlas may be modified to increase the probability of a successful classification of a tissue group.

In another embodiment, said atlas may comprise anatomical information that may be transferred to the acquired image. The anatomical information may be provided in the form of labels identifying a specific tissue group. The labels may be provided to selected volume elements of a tissue group in the atlas. The labels may be transferred to the acquired image to provide selected volume elements in the acquired image with the label. A step of classifying volume elements in a tissue volume may comprise a step of transferring labels for selected volume elements in the tissue volume in the acquired image to all volume elements in said tissue volume. An automated process for classifying a tissue volume, such as a muscle tissue volume or a breast volume, for defining the region of interest may thereby be provided.

In a further embodiment, the step of non-rigid registration may comprise a step of separately registering multiple atlases to the acquired image. By registering multiple atlases on the acquired image, a more robust segmentation of the acquired image may be provided. Atlases with different organ composition, thereby representing a plurality of anatomical variations, may be used simultaneously. The result of the segmentation may thereby be improved.

In one embodiment, the results of the segmentation using the multiple atlases may be added to the acquired image to form a map, wherein said map may be normalized to form a probability map defining the probability that a volume element in the acquired image represents tissue. In a further embodiment, the normalization may provide a value between 0 and 1 for volume elements in the acquired image, wherein the value 1 represents that all of the multiple atlases define that volume element as tissue, and the value 0 that none of the multiple atlases define the volume element as tissue. For each volume element, a probability value may be provided defining the probability of said volume element belonging to a specific tissue group.

In a yet further embodiment, the step of classifying volume elements may comprise a step of labeling volume elements in the acquired image to a tissue group based on the probability map. Volume elements determined to belong to a tissue group based on the probability map may thereby be labeled to that tissue group. Such classification of volume elements may then be a basis for the quantification of the lean tissue volume of the tissue group.

In another embodiment, said step of labeling volume elements may comprise a step of applying a threshold of number of atlases that need to classify a specific volume element to a tissue group in order to label that volume element to said tissue group. Thereby, if a number of atlas-based segmentations above the threshold define a volume element as belonging to the tissue group, the volume element may be provided with the corresponding label. The threshold may in one embodiment be 50% of the atlases.

In one embodiment, a threshold of number of atlases may be selected for a first tissue group which defers from a threshold selected for a second tissue group. A too high threshold may lead to an underestimation of the muscle tissue volume, and a too low threshold may lead to an overestimation of the muscle tissue volume. The optimal threshold may be different for different tissue groups. Hence, different thresholds may be used for different tissue groups.

In another embodiment, the step of non-rigid registration may comprise a step of selecting, from a group of atlases, one or more atlases that may comprise the most similar organ tissue volume to the acquired image. When using multiple atlases, a selection operation may be performed wherein the atlases are compared to the acquired image, and a number of atlases having a certain amount of similarity in body muscle volume are selected. Each atlas may be given a value representing its similarity with the acquired image. Atlases having such value above a threshold may be selected.

In a further embodiment, said step of selecting one or more atlases may be repeated in an iterative process, wherein the atlases selected in a first selection process may be used as basis for selection in a second selection process. The atlases selected in the first selection process may thereby be evaluated again. The number of atlases may further be reduced in the second selection process, thereby only selecting the best matching atlases. The performance of the segmentation of the acquired image may thereby be further improved.

In a further embodiment, the step of quantifying the muscle tissue volume may comprise a calculation derived from the normalized water volume minus the normalized fat volume for the volume elements in the muscle tissue volume.

In a further embodiment, the calibrated fat image, the soft tissue mask and the region of interest may all be defined over a common value range. Each volume element in the calibrated fat image, the soft tissue mask and the region of interest may respectively have values in the common value range. For the calibrated fat image, the range may extend from an end point representing no fat to an end point representing pure fat. Similarly, for the soft tissue mask the range may extend from an end point representing no soft tissue to an end point representing pure soft tissue. Further, for the region of interest the range may extend from an end point representing volume element to be excluded to an end point representing volume element to be included. Similarly, the calibrated water image may be defined over the common value range. For the calibrated water image, the range may extend from an end point representing no water to an end point representing pure water.

Such common value range may in one embodiment be between 0 and 1, [0, 1]. A common value range provides that the lean tissue volume quantification may be calculated without calibration problems.

BRIEF DESCRIPTION OF THE DRAWINGS

The invention will in the following be described in more detail with reference to the enclosed drawings, wherein.

DESCRIPTION OF EMBODIMENTS

Figure 1:
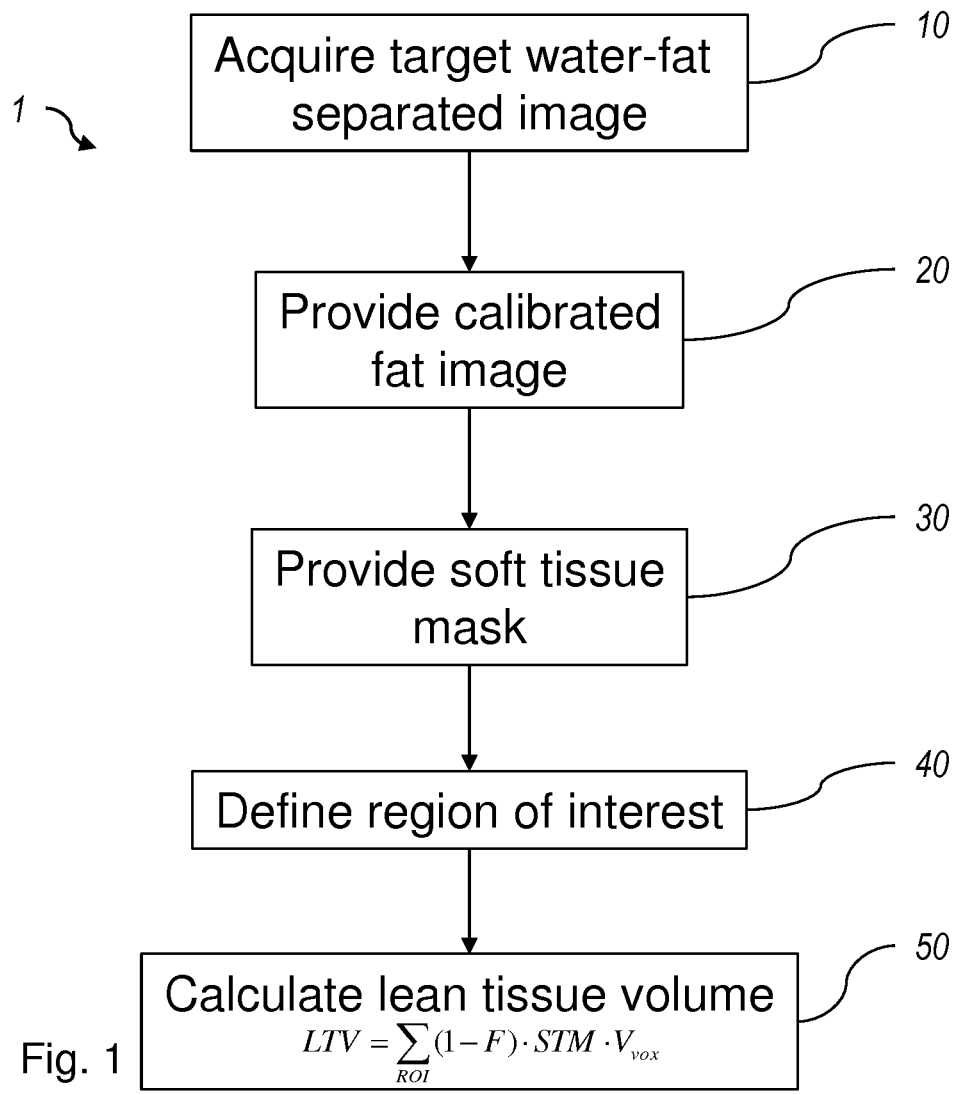
FIG. 1 is a flow chart of a method according to an embodiment of the present invention.

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

As illustrated in FIG. 1, the method of quantifying a lean tissue volume according to an embodiment of the present invention comprises five main steps.
a) Acquisition (10) of a water-fat separated image.
b) Providing (20) a calibrated fat image.
c) Providing (30) a soft tissue mask.
d) Defining (40) a region of interest in the acquired image.
e) Calculating (50) a lean tissue volume.

The method illustrated in FIG. 1 can be described as:

$$LTV = \sum_{ROI} (1-F) \cdot STM \cdot V_{vox},$$

where LTV is the lean tissue volume, F is the calibrated fat image, STM is the soft tissue mask, $V_{vox}$ is the volume of each voxel and ROI is the voxels in the region of interest. The defining of the region of interest can be made manually or automatically.

Figure 2:
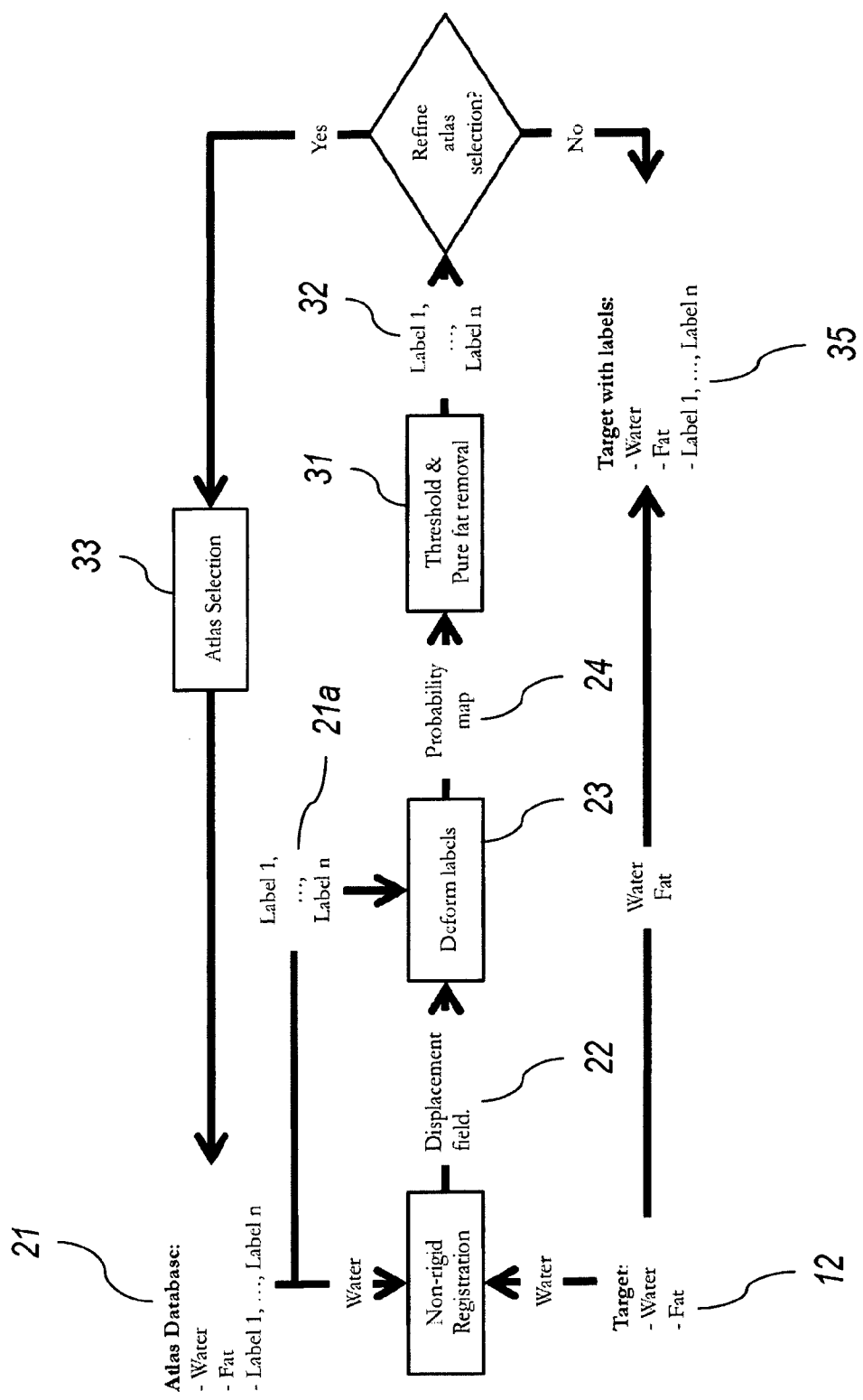
FIG. 2 is a flow chart of method steps according to an embodiment of the present invention.

The steps a)-d) of method will be described in more detail below with further reference to FIG. 2.

The method requires water-fat separated images with quantitative fat information. For the present embodiment, two or multiple point Dixon imaging, with phase-sensitive reconstruction, is used to acquire 10 the water-fat separated images. There are, however, several other separation methods that may be used. Such other methods which provide fat images to be used for providing a calibrating fat image are disclosed in:

Berglund J, Ahlstrom H, Johansson L, Kullberg J. Two-point Dixon method with flexible echo times. Magnetic resonance in medicine:official journal of the Society of Magnetic Resonance in Medicine/Society of Magnetic Resonance in Medicine 2011; 65(4):994-1004.

Berglund J, Kullberg J. Three-dimensional water/fat separation and T2* estimation based on whole-image optimization—application in breathhold liver imaging at 1.5 T. Magnetic resonance in medicine:official journal of the Society of Magnetic Resonance in Medicine/Society of Magnetic Resonance in Medicine 2012; 67(6):1684-1693.

Hernando D, Haldar J P, Sutton B P, Ma J, Kellman P, Liang Z P. Joint estimation of water/fat images and field inhomogeneity map. Magnetic resonance in medicine: official journal of the Society of Magnetic Resonance in Medicine/Society of Magnetic Resonance in Medicine 2008; 59(3):571-580.

Ma J. Dixon techniques for water and fat imaging. Journal of magnetic resonance imaging: JMRI 2008; 28(3): 543-558.

Reeder S B, Pineda A R, Wen Z, Shimakawa A, Yu H, Brittain J H, Gold G E, Beaulieu C H, Pelc N J. Iterative decomposition of water and fat with echo asymmetry and least-squares estimation (IDEAL): application with fast spin-echo imaging. Magnetic resonance in medicine:official journal of the Society of Magnetic Resonance in Medicine/Society of Magnetic Resonance in Medicine 2005; 54(3):636-644.

Yu H, McKenzie C A, Shimakawa A, Vu A T, Brau A C, Beatty P J, Pineda A R, Brittain J H, Reeder S B. Multiecho reconstruction for simultaneous water-fat decomposition and T2* estimation. Journal of magnetic resonance imaging: JMRI 2007; 26(4):1153-1161.

The acquired image comprises a water image and a fat image. A method to calibrate a fat image based on pure adipose tissue as an internal intensity reference, i.e. the signal intensity level in a given fat image voxel, i.e. volume element, is related to the intensity in pure adipose tissue which is given the value 1, corresponding to 100% adipose tissue. In addition to creating a calibrated fat image, the method also removes some of the inhomogeneity in the original water image.

The method according to an embodiment of the present invention uses an atlas-based registration and segmentation for defining the region of interest. Alternatively, the region of interest can be manually defined, or automatically defined with another method.

The starting point for an atlas-based segmentation method is the generation of the atlas 21. An atlas 21 is here defined as a water and fat image pair with corresponding labels 21a defining different tissue groups. The atlas 21 is then registered onto an acquired (target) image 12. The intention of the registration is that the atlas 21 should be as similar to the acquired image 12 as possible. For this task, the water image of the atlas 21 is used, since it displays the least anatomical variation and contains the most information regarding tissue volume shape. A multi-scaled and phase-based method, such as a morphon method, is used for the non-rigid registration 20. The morphon registration iteratively estimates a displacement field 22 by applying directional quadrature filters on the atlas 21 and the acquired image 12 and updates the displacement field such that the phase differences between the filter responses is minimized. After the convergence of the morphon, the resulting displacement field 22 consists of an information map, and the anatomical information, such as the labels 21a defining muscle groups, can be transferred 23 from the atlas 21 to the acquired image 12.

The robustness of the atlas-based segmentation is improved by registering multiple atlases 21 to the acquired image 12. Multiple atlas registration allows simultaneous usage of atlases 21 with different body composition, representing a plurality of anatomical variations, which may improve the segmentation operation. The registration is therefore made for each atlas and the suggested labels are added to each other on the target, forming a map. The map is normalized and used as a probability map 24. A value equal to 1 for a voxel provides that all atlases classify a voxel as tissue, and a value equal to zero provides that none of the atlases classifies that voxel as tissue.

The third step of the method is to classify the label of each voxel based on the resulting probability map 24 from the multiple atlas registration. A threshold 31 is applied that determines how many atlases 21 that must agree to classify a voxel as a certain muscle. Too high a threshold would lead to an underestimation of the tissue volume, while too low a threshold would instead lead to an overestimation. Different tissue groups have different surroundings, so optimal thresholds for each group may be used.

The optimal thresholds 31 for each segmented tissue group may be calculated by finding the threshold that maximize the similarity between a ground truth segmentation and the automatic segmentation, based on the Similarity Index (SI), also known as the Dice coefficient. The threshold value that provided the highest mean SI (over all atlases used) was used as the optimal threshold value.

The probability of achieving a good registration result is higher if the atlas 21 and the target image 12 are similar. An automated selection of finding atlases with similar tissue distribution can in one embodiment be used to improve the segmentation result. This is implemented as an iterative process. After the first iteration, where a random or general subset of atlases is used, a second iteration 33 is performed where only the atlases 21 with the most similar tissue volume, compared to the result from the first iteration, are used for a second round of voting. Instead of the criteria of most similar whole body muscle volume, another feature describing the subjects may be used.

After the tissue classification an acquired image 35 with tissue group labels 32 is provided.

Figure 3:
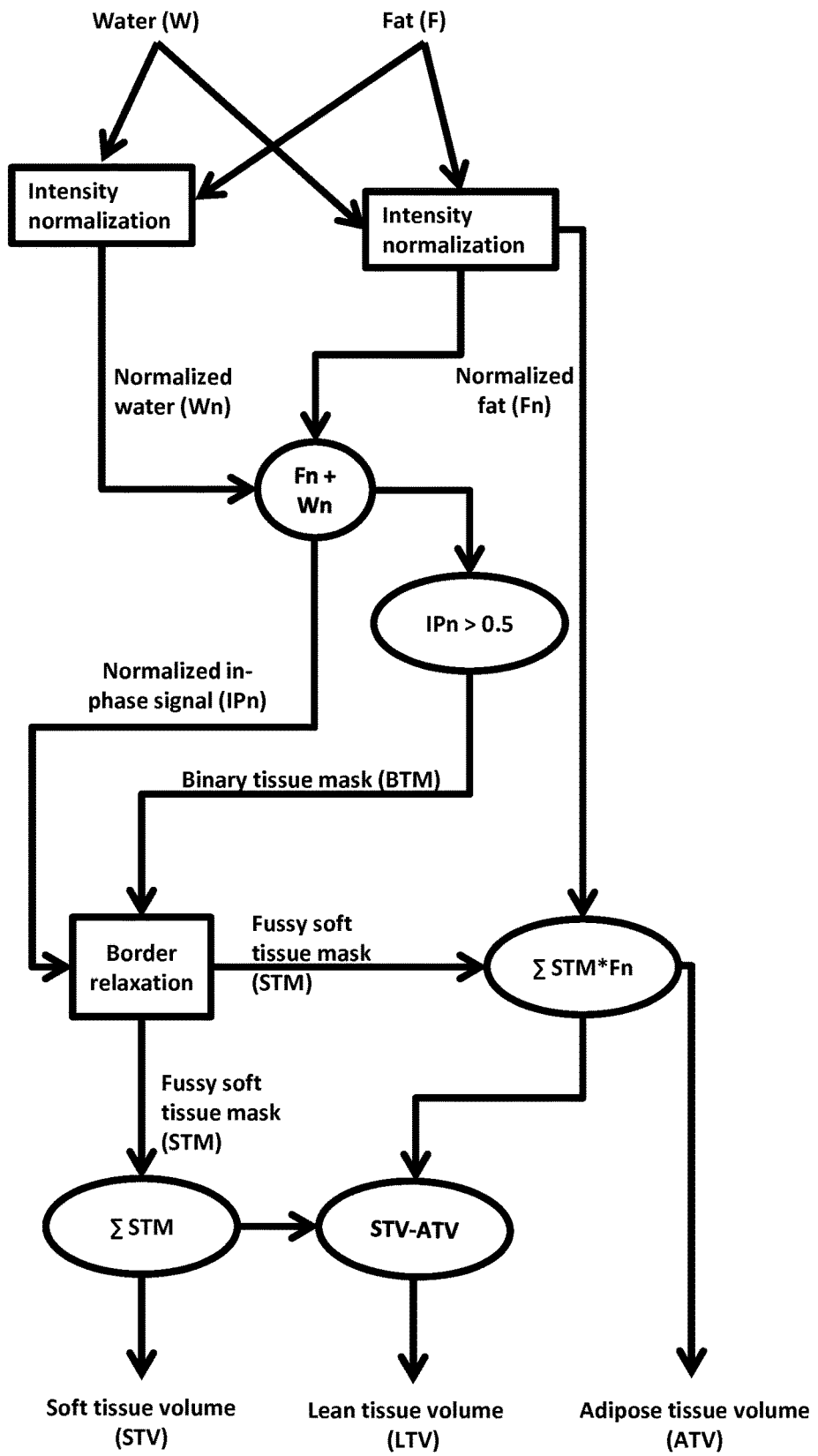
FIG. 3 is a flow chart of a quantification method according to an embodiment of the present invention.

The final step to obtain the tissue volume is to combine the result from the tissue segmentation and classification steps with image information present in the tissue volume in the acquired image. This is described below with reference to FIG. 3.

One step of the lean tissue volume calculation consists of removal of voxels not belonging to the body in the acquired image 35, i.e. background removal. Only voxels inside a fuzzy soft tissue mask (STM) are included in order to reduce noise from voxels in the background. First, a binary tissue mask (BTM) is created by calibrating the water tissue volume (Wn), similar as described for the fat tissue volume above providing a calibrated fat tissue volume (Fn). A calibration of the water image is based on pure water as an internal intensity reference. I.e. the signal intensity level in a given water image voxel is related to the intensity in pure water tissue which is given the value 1, corresponding to 100% water tissue. Water image voxels with an intensity of no water is given the value 0.

The sum (Fn+Wn) of the normalized water tissue volume and the fat tissue volume provides a normalized in-phase signal (IPn). A threshold is applied to the normalized in-phase signal. The threshold is at a level of 0.5. The fuzzy tissue mask is created by setting the voxels within one voxel from the borders of the binary body mask equal to the sum of the normalized water and fat images. This operation is referred to as a border relaxation. By using the fuzzy soft tissue mask, the partial volume effects on the volume measurement are minimized.

The volume of the segmented tissue mask, $M_M$, is calculated by:

$$M_M = \sum_{ROI} (M_{AUT} \cdot STM) \cdot V_{vox}$$

where $M_{AUT}$ is the automatic tissue segmentation, STM is the soft tissue mask, $V_{vox}$ is the volume of each voxel and ROI is the voxels in the region of interest. This provides a quantification of the tissue in the classified volume, also described as soft tissue volume (STV). Based on the same fuzzy soft tissue mask and the calibrated fat tissue volume, a quantification of fat tissue volume, or adipose tissue volume (ATV), is provided.

The step of quantification of lean tissue volume corrects for fatty infiltration in $M_{AUT}$.

This is performed by a calculation 50 of the lean tissue volume, LTV:

$$LTV = \sum_{ROI} (1 - F) \cdot M_{AUT} \cdot STM \cdot V_{vox}$$

where F is the calibrated fat image, $M_{AUT}$ is the automatic tissue segmentation, STM is the soft tissue mask, $V_{vox}$ is the volume of each voxel and ROI is the voxels in the region of interest.

The calibrated fat image provides a continuous fat image. The fat signal level in each voxel classified as, for instance, muscle tissue is subtracted from the final tissue volume calculation. LTV removes regions containing pure adipose tissue, i.e. fatty streaks and subcutaneous tissue. Further, in the presence of diffuse fat infiltration, LTV quantifies the amount of muscle tissue rather than the volume of muscle tissue plus diffuse fat infiltration. This provides a quantification of lean tissue volume (LTV).

Figure 4A:
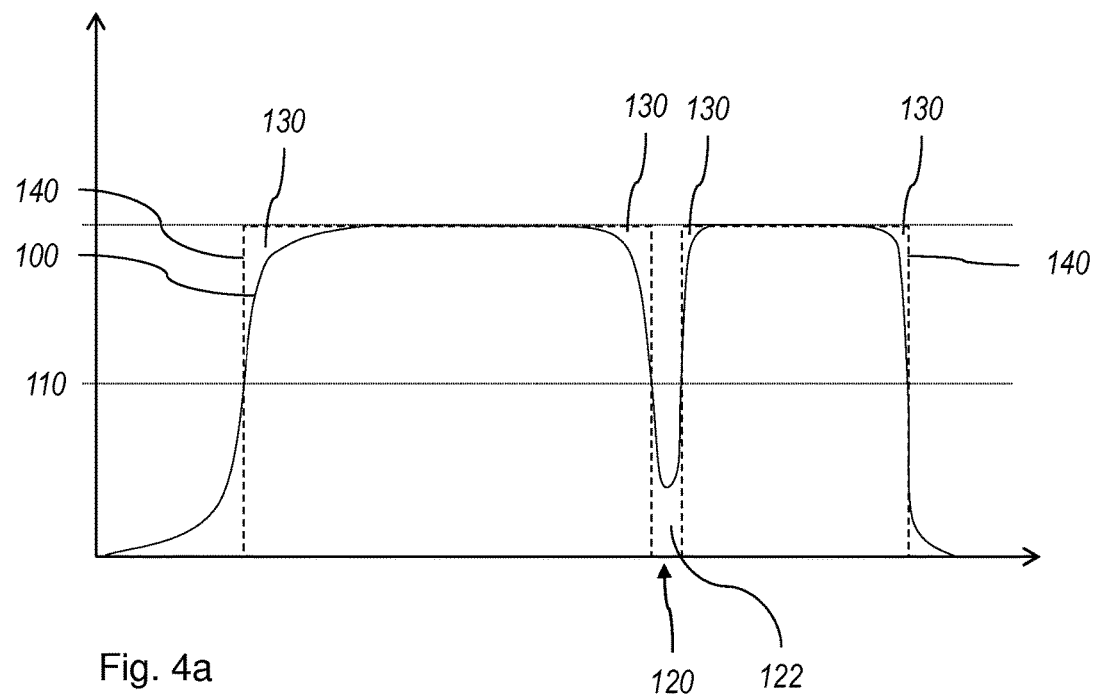
FIGS. 4a and 4b are two-dimensional chart representations of a muscle tissue volume.
Figure 4B:
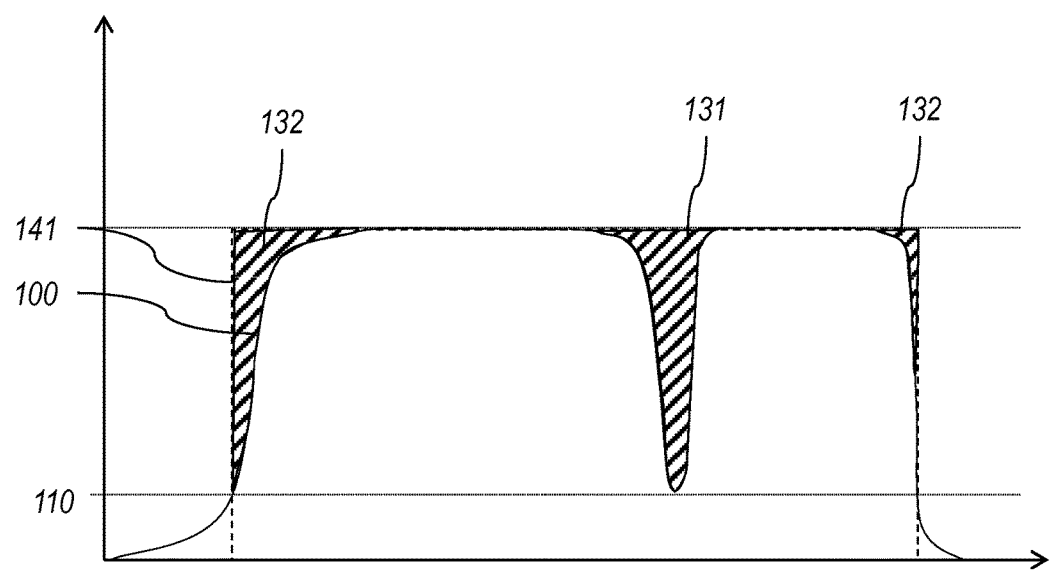

This is further illustrated in FIGS. 4a and 4b, which illustrate a two-dimensional representation of a muscle tissue volume 100 (y axis). A low representation of muscle tissue at a voxel on the x axis provides a corresponding level of fat. FIG. 4a illustrates a known step of quantifying muscle tissue wherein a threshold 110 is set. Voxels with muscle tissue signal level below the threshold 110, i.e. with a fat signal level above the threshold 110, are removed from the quantified muscle tissue volume 140. A portion 120 of the voxels, within the outer boundaries of the muscle tissue volume 100, will be removed from the quantification 140 due to a classification as pure fat infiltration. However, muscle tissue 122 in such voxels will also be removed and thereby remove such tissue 122 from the quantification 140 of the muscle tissue volume. Further, diffuse fat infiltration 130 will be quantified as muscle tissue due to the low amount of fat.

FIG. 4b illustrates the quantification step according to the present invention, wherein quantification of the muscle tissue volume 100 is determined by subtracting the fat level 131, 132 in the voxels classified within the muscle tissue volume 100 from the corresponding muscle tissue signal level (water signal level). The threshold 110 may thereby be set lower, or even nullified, to provide a more correct quantification of the muscle tissue volume. The (high) fat levels 132 at the boundaries will anyhow be removed by the subtraction operation. A large fat infiltration 131 will further be removed from the quantification, even with a lower threshold 110. At the same time, the muscle tissue present in the voxels 120 having large fat infiltration is also part of the muscle tissue quantification 141.

Figure 5:
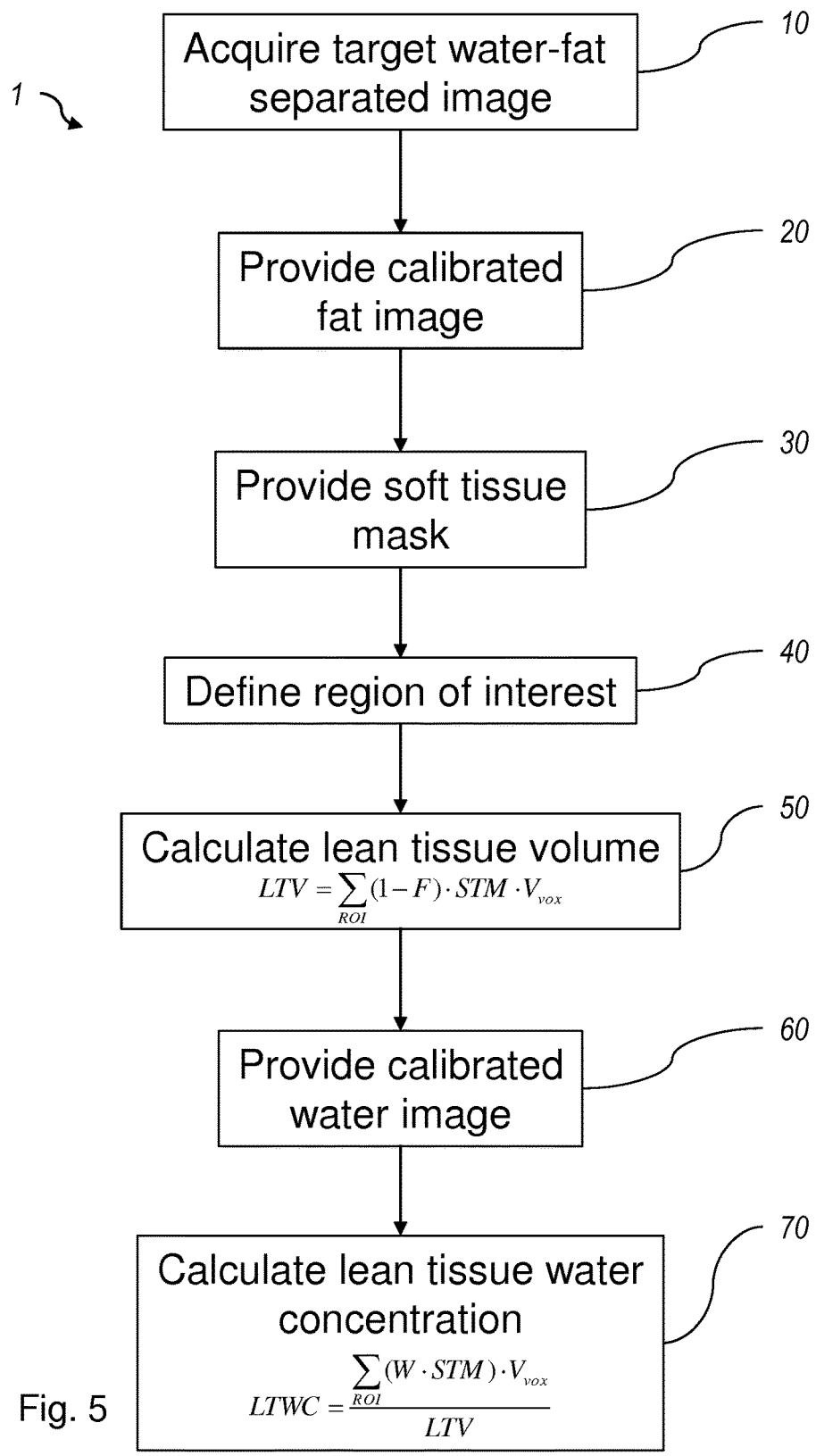
FIG. 5 is a flow chart of a method according to an embodiment of the present invention.

According to the embodiment illustrated in FIG. 5, the method 1 of the present invention may further comprise a step of providing 60 a calibrated water image and a step of calculating 70 a lean tissue water concentration (LTWC). The calculation of lean tissue water concentration may be described as:

$$LTWC = \frac{\sum_{ROI}(W \cdot STM) \cdot V_{vox}}{LTV},$$

where W is the calibrated water image, STM is the soft tissue mask, LTV is the calculated lean tissue volume, $V_{vox}$ is the volume of each voxel and ROI is the voxels in the region of interest. The lean tissue water concentration provides an effective water concentration as a ratio of the total water and fat in the region. The lean tissue water concentration includes measured water signal level in the region of interest of the acquired image and not water or other tissue not magnetic resonance visible in the region of interest.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A method of quantifying a lean tissue volume comprising the steps of acquiring an image, by a magnetic resonance imaging device, as a water-fat separated magnetic resonance image, wherein the acquired image comprises a water image and a fat image each comprising a plurality of volume elements, each volume element in the water image comprising a water signal level and each volume element in the fat image comprising a fat signal level, generating a calibrated fat image from the fat image using pure adipose tissue as an intensity reference, providing a soft tissue mask defining areas of soft tissue in the acquired image, defining a region of interest of the acquired image, and calculating a lean tissue volume by multiplying, for each volume element in the region of interest, the soft tissue mask with the volume of each volume element and the result of one minus the calibrated fat image, and summarizing the products of said multiplications for all volume elements in the region of interest, wherein an increased accuracy of a quantification of the lean tissue volume is provided by removing the fat signal level from the water signal level in those volume elements classified within the region of interest.

2. The method according to claim 1, further comprising a step of providing a calibrated water image and a step of calculating a lean tissue water concentration by multiplying, for each volume element in the acquired image, the soft tissue mask with the calibrated water image and the volume of each volume element, determining a sum of the products of said multiplications for all volume elements in the region of interest, and divide said sum with said calculated lean tissue volume.

3. The method according to claim 1, wherein the step of providing a soft tissue mask comprises a step of removing volume elements that does not contain magnetic resonance visible tissue, wherein the step of removing volume elements comprises the steps of providing a calibrated water image, applying a threshold to the sum of the calibrated fat image and the calibrated water image, wherein volume elements above said threshold forms a binary tissue mask, and forming a fuzzy soft tissue mask by setting the volume elements within one volume element from the borders of the binary tissue mask equal to the sum of the normalized water and fat images.

4. The method according claim 1, wherein the step of defining a region of interest comprises a step of non-rigid registration of at least one atlas to the acquired image to segment the acquired image.

5. The method according to claim 4, wherein the step of non-rigid registration comprises a step of multi-scaled and phase-based registration, such as a morphon registration, of said atlas.

6. The method according to claim 4, wherein said atlas comprises anatomical information that is transferred to the acquired image.

7. The method according to claim 6, wherein the results of the registration of the multiple atlases are added to the acquired image to form a map, wherein said map is normalized to form a probability map defining the probability that a volume element in the acquired image represents muscle tissue, and wherein the normalization provides a value between 0 and 1 for volume elements in the acquired image, wherein the value 1 represents that all of the multiple atlases define that volume element as muscle tissue, and the value 0 that none of the multiple atlases define the volume element as muscle tissue.

8. The method according to claim 7, wherein the method further comprises a step of classifying volume elements in the water image as a tissue group based on said at least one atlas, wherein said step of classifying comprises a step of labeling volume elements in the acquired image to a tissue group based on the probability map.

9. The method according to claim 8, wherein said step of labeling volume elements comprises a step of applying a threshold of number of atlases that need to classify a specific volume element to a tissue group in order to label that volume element to said tissue group.

10. The method according to claim 9, wherein a threshold of number of atlases is selected for a first tissue group which defers from a threshold selected for a second tissue group.

11. The method according to claim 4, wherein the step of non-rigid registration comprises a step of separately registering multiple atlases to the acquired image.

12. The method according to claim 4, wherein the step of non-rigid registration comprises a step of selecting, from a group of atlases, one or more atlases that comprise the most similar tissue volume to the acquired image, and wherein said step of selecting one or more atlases is repeated in an iterative process, wherein the atlases selected in a first selection process are used as basis for selection in a second selection process.

13. The method according to claim 1, wherein the calibrated fat image, the soft tissue mask and the region of interest all are defined over a common value range.

14. The method according to claim 13, wherein the common value range extends from 0 to 1.

15. The method of claim 1, wherein the region of interest comprises one of a specific organ, a muscle, a muscle group or a breast, the quantification of the lean tissue volume indicating a condition of the region of interest.

* * * * *